United States Patent [19]

Masson et al.

[11] 4,283,383

[45] Aug. 11, 1981

[54] ANALYSIS OF BIOLOGICAL FLUIDS

[75] Inventors: Pierre L. Masson, Brussels; Joseph F. Heremans, Leuvain, both of Belgium

[73] Assignee: Technicon Instruments Corporation, Tarrytown, N.Y.

[21] Appl. No.: 946,173

[22] Filed: Sep. 27, 1978

Related U.S. Application Data

[62] Division of Ser. No. 578,699, May 19, 1975, Pat. No. 4,143,124.

[30] Foreign Application Priority Data

May 20, 1974 [GB] United Kingdom .............. 22377/74

[51] Int. Cl.³ ............................................. G01N 33/54
[52] U.S. Cl. .................... 424/12; 23/230 R; 23/230 B; 424/1.5; 424/8; 424/11; 424/13; 435/7
[58] Field of Search .................... 424/1, 1.5, 8, 11, 12, 424/13; 23/230 R, 230 B; 435/7

[56] References Cited

U.S. PATENT DOCUMENTS

| 3,639,558 | 2/1972 | Csizmas | 424/12 |
|---|---|---|---|
| 3,639,559 | 2/1972 | Tax | 424/12 |
| 4,062,935 | 12/1977 | Masson | 424/12 |
| 4,143,124 | 3/1979 | Masson | 424/12 |

OTHER PUBLICATIONS

Haupt, Hoppe-Seyler's Z. Physiol. Chem., vol. 353, Jul. 1972, pp. 1126-1132.
Agnello, Chem. Abs., vol. 74, 1971, Ab. No. 21475b.
Agnello, J. Exp. Med., vol. 134, 1971, pp. 228s-241s.
Nydegger, Chem. Abs., vol. 81, 1974, Ab. No. 36322t.
Nydegger, Chem. Abs., vol. 83, 1975, Ab. No. 6874y.
Volanakis, Chem. Abs., vol. 81, 1974, Ab. No. 48438y.
Franklin, J. Exp. Med., vol. 105, 1957, pp. 425-438.
Edelman, J. Exp. Med., vol. 108, 1958, pp. 105-120.

Primary Examiner—Anna P. Fagelson
Attorney, Agent, or Firm—S. P. Tedesco

[57] ABSTRACT

Biological fluids, such as serum, are analyzed for the presence, nature and/or amount of antibodies, antigens and antibody:antigen complexes therein using as a reagent, insolubilized rheumatoid factor or insolubilized C1q. These reagents are themselves novel. They bind to antibody:antigen complexes, but not to free antibodies or antigens, and complexes can thus be removed from mixtures thereof with other materials, such as antibodies and antigens.

16 Claims, No Drawings

ANALYSIS OF BIOLOGICAL FLUIDS

This is a division of application Ser. No. 578,699, filed May 19, 1975, now U.S. Pat. No. 4,143,124.

This invention is concerned with the analysis of biological fluids, such as urine or serum, for the determination of the presence, amount and/or nature of antibodies, antigens and antibody:antigen complexes, and with novel materials useful therefor. (For simplicity hereinafter the symbols "Ab", "Ag" and "Ab:Ag" are used for "antibody", "antigen", and "antibody-antigen complex", respectively.)

As is well known, it is important to be able to analyse biological fluids for Ab, Ag and Ab:Ag complexes. For example many diseases are characterized by the presence in the circulation of Ab:Ag complexes. The Ag may be any of a wide variety of proteins including those due to the presence of bacteria or viruses or those released from human tissues or cancer cells. The Ab are, of course, specific to the particular Ag and are predominantly immunoglobulins of the IgG class synthesised by the subject's lymphoid system. The detection of Ab:Ag complexes in blood, and their separation and characterisation, provide information of value and can be used, for example, in the diagnosis of disease.

There are a number of techniques known for detecting and quantifying Ag, Ab and Ab:Ag complexes and particularly for determining the nature and amount of Ag present. These quantification techniques are called "immunoassay" procedures.

It has been known for some time that two naturally occurring substances, namely rheumatoid factor (RF) and a particular component of complement, namely Clq, have the property of combining with Ab:Ag complexes but not with either free Ag or free Ab. Whilst there has been a prior proposal (Agnello et al., J. Exp. Med., 134, 228,1971) to use this property in one particular way for the detection (but not the quantitative assay or absolute determination) of Ab:Ag complexes, it has never previously been realised that RF and Clq are potentially extremely useful reagents in the analysis of Ab, Ag and Ab:Ag complexes.

We have now found that RF and Clq in insolubilised form are in fact very widely applicable reagents in analytical procedures involving Ab, Ag and/or Ab:Ag complexes and their use can, for example, simplify and render more accurate immunoassay techniques.

RF is a known material and methods for its preparation and isolation are known. It is present, or can be made to appear, in the blood of a number of animal species including man. It is normally obtained from goats or rabbits by intradermal injections of their own purified immunoglobulins previously aggregated by heating at about 63° C. for about 10 minutes. RF is then isolated from the serum obtained from the animals, by passing the serum through a column of aggregated immunoglobulins on which it is retained. The RF can then be eluted from the column using as eluant a solution of the appropriate pH or salt concentration.

Clq is a natural circulating protein and methods for its separation and purification are known. It is usually obtained from human, rabbit or bovine serum by a technique known as "euglobulin precipitation" which is described in, for example, J. Immunol., 106 304-413 (1971).

In one aspect, the invention provides, as analytical reagents, RF and Clq in insolubilised form. By "insolubilised" RF and Clq, we mean that the RF or Clq is covalently bonded to a solid phase substrate which is insoluble in aqueous fluids, or is adsorbed on a synthetic solid phase substrate which is insoluble in aqueous fluids, one example of such a synthetic solid phase substrate being latex.

Insolubilisation of RF and Clq may be effected by covalently linking the RF or Clq directly or indirectly to a solid phase. The general procedures known and used for covalently coupling proteins to insoluble substrates can be used for insolubilising RF and Clq. The solid phase substrate must contain one or more reactive groups, such as amino or carboxylic groups, for the coupling reaction. Suitable solid phase substrates include naturally occurring materials such as aggregated immunoglobulins, and synthetic materials, such as aminated agarose.

In some cases, the RF or Clq can be directly covalently linked to or absorbed on the solid phase, e.g. where the solid phase is nylon, agarose, cellulose, acrylamide or acrylic polymers, polystyrene or various glass preparations. It is generally preferred, however, to link the RF or Clq to the solid phase using a bridging substance such as glutaraldehyde. A preferred reagent of the invention is RF or Clq covalently linked by a glutaraldehyde bridge to aminated agarose.

Where RF or Clq are insolubilised by adsorbtion on a synthetic solid phase substrate, this may be effected by contacting a solution of RF or Clq with the solid phase, for example.

It is generally preferred that the reagents of the invention be in particulate or granular form, such as beads of aminated agarose having thereon a coating or RF or Clq. However, for some purposes, e.g. continuous flow analysis, it is advantageous to form the reagents as a coating over at least part of the inner surface of a tube, so that reactants passing through the tube come into contact with the reagent coating.

It is known to isolate RF from serum by passing the serum through a column of aggregated immunoglobulins, on which the RF is retained. In such a column, the RF is temporarily adsorbed on the aggregated immunoglobulins and is not covalently linked thereto. It will be appreciated that aggregated immunoglobulins are not synthetic materials.

The insolubilised RF and Clq reagents of the invention have a very large number of uses in biological analyses. Basically, all these uses depend on the ability of the reagents to combine with Ab:Ag complexes and not with free Ab and free Ag, thereby making it possible to use the reagents to separate Ab:Ag complexes from mixtures thereof with free Ab and free Ag.

The reagents of the invention can be used to particular advantage in continuous flow analysis of biological fluid samples, and the invention includes such use.

In order that the invention may be more fully understood, various test procedures utilising a reagent of the invention will now be described by way of illustration only.

SEPARATION

The procedure for separating Ab:Ag complexes from biological (or other) fluids is to contact the fluid with insolubilised RF or Clq. The complexes in the fluid will become bound to the insolubilised RF or Clq, whereas other materials present, such as Ab or Ag, will not (or will not to any significant degree). Hence, by separating the insolubilised RF or Clq from the mixture, the Ab:Ag are separated out bound on the RF or Clq. They can then, if desired, be separated from the insolubilised RF or Clq by washing with a suitable buffer of appropriate salt concentration and pH. In this way, a relatively concentrated solution of the complex(es) can be obtained.

This procedure can conveniently be carried out using a column containing the insolubilised RF or Clq. The serum or other sample containing an Ab:Ag complex is passed through the column and the complex is retained therein bound to the RF or Clq. The complex can then be eluted. In one typical procedure, a micro-column comprising beads of aminated agarose to which Rf or Clq has been coupled with glutaraldehyde, is used. The serum is passed through the column and the retained Ab:Ag complexes subsequently eluted using, for example, increasing concentrations (1 M to 3 M) of ammonium thiocyanate.

As an alternative to using a column, insolubilised RF or Clq can simply be mixed, for example in a flask, with the test liquid and then subsequently separated by centrifuging or filtering.

The separative processes of the invention are useful not only for Ab:Ag complexes but also, indirectly, for separating particular Ab or Ag from solutions. For example, if it is desired to separate an antigen Ag' from a solution, the specific antibody Ab' may be added in excess to form the complex Ab':Ag' which may then be separated using a reagent of the invention. If the initial solution contains an Ab:Ag complex, this must usually first be separated out by a preliminary treatment, before the specific antibody Ab' is added.

A particular feature of these separative procedures of the invention is that they are very efficient and so allow the collection, and concentration, of Ab:Ag complexes from very dilute solutions thereof. This is a very important advantage since not infrequently the complexes are present in very low concentrations in sera or other biological fluids, and it is extremely difficult by prior known procedures, to separate these complexes.

SEPARATIVE DETECTION AND QUANTITATION (a) This test involves selective removal of Ab:Ag complexes from a biological fluid by contacting the fluid with insolubilised RF or Clq (as described above) followed by detection of the complexes. For example, a sample of serum is treated to separate out any Ab:Ag complexes therein by binding them to insolubilised RF or Clq. Any complexes so bound are then freed from the RF or Clq and detected, for example by using soluble RF or Clq. Thus, when red blood cells (or particles coated with immunoglobulins) contact soluble RF or Clq, agglutination begins to occur, but if there is also present in solution an Ab:Ag complex, this will react with the RF or Clq relatively quicker and the RF and Clq will become bound to the Ab:Ag complex in solution and, as a result, no agglutination of the coated particles (or red blood cells) will occur. Thus, the presence of Ab:Ag complexes in a liquid, for example, can be detected by contacting the serum with (soluble) RF and Clq and with particles coated with immunoglobulins. If agglutination is observed, the serum does not contain any Ab:Ag complexes. This novel technique is more fully described in our copending application no.

(b) This test can also be useful for detecting the presence of a particular Ab or Ag, in a sample. For example, when testing for a particular antigen, Ag', there is first added to the serum the appropriate specific antibody Ab', and then the mixture is contacted with a reagent of the invention to separate out any complexes therein. The presence of any such complexes may then be detected as in (a) above. If the serum sample originally contains other Ab:Ag complexes, these can be removed before adding the Ab'.

(c) Another detection procedure involves competition between two Ab:Ag complexes for a limited about of RF or Clq. Thus, for example, if an excess of a labelled Ab:Ag complex is added to a limited amount of insolubilised RF or Clq, then all the RF or Clq will become bound to the complex. If, then, in addition to the labelled complex, a serum sample is added containing unlabelled Ab:Ag complex, the labelled and unlabelled complex will compete on molar terms for the limited amount of RF or Clq. If, after equilibrium is reached, the RF or Clq is removed, together with the complexes bound thereto, the presence (or the presence of a particular minimum amount) of labelled complex in the remaining solution indicates that the serum sample contained an Ab:Ag complex. This method can be operated quantitatively to measure the amount of complex in the serum sample.

This technique may also be used generally as described above, for detecting the presence of a particular Ag or Ab.

(d) A further detection procedure (which may be operated quantitatively), especially for a particular Ag or Ab, is as follows. If it is wished to establish whether a sample of serum, for example, contains particular antigen Ag', the specific antibody Ab' is prepared and labelled with, for example, an enzyme. The labelled Ab' is then mixed with insolubilised RF or Clq, and the serum sample added thereto. The insolubilised RF or Clq (with the adhering Ab':Ag' complexes) is then separated out and the remaining liquid tested for the presence (or amount) of labelled Ab' therein. If this is less than the amount originally added, the specific antigen Ag' must have been present in the serum sample. As an example, one can detect the presence (or absence) of a specific Ag, for example IgE, in serum as follows. Anti-IgE antibodies, labelled with catalase, are added to insolubilised RF or Clq (e.g. agarose beads), in an amount in excess of that required to complex with any IgE in the sample to be tested. The serum sample is then added and the mixture incubated. After separation of the insolubilised RF or Clq (carrying with it any IgE: anti IgE complexes formed), the residual enzymatic activity of the remaining liquid can be measured. If IgE is present in the serum sample, this residual enzymatic activity will be less than the original activity of the added anti-IgE antibodies since some of the latter will have complexed with the IgE in the serum and been removed with the insolubilised RF. This method can be carried out quantitatively to determine the amount of IgE in the serum.

Another example of this general procedure concerns the detection of, for example, the antigen morphine. In this procedure, morphine is labelled with an enzyme, eg. amylase. Specific anti-morphine antibodies, Ab" are prepared. The sample of serum or urine, for example, to be tested for morphine, is mixed with the Ab". Any morphine present will form a complex with the Ab". There is then added the enzyme-labelled morphine. This will only be able to complex with the Ab" in proportion to the concentration of morphine in the serum or urine.

Insolubilised RF or Clq is added to absorb the Ab:Ag complexes formed between the Ab" and the morphine in the serum, and between the Ab" and the labelled morphine. The insolubilised RF or Clq (carrying with it these complexes) is then removed from the solution. There remains in solution labelled morphine and by measuring its enzymatic activity, it is possible to determine whether or not the original serum sample contained morphine and, if it did, how much morphine was present.

It will be appreciated that whilst the above example refers only to morphine, the same procedure can be used for the detection of other antigens, and *mutatis mutandis* antibodies. The labelling need not be enzymatic.

(e) The reagents of the invention are also useful in nephelometric immunoassays, in particular to improve the sensitivity of such assays. In particular, the use of insolubilised RF and Clq has greatly facilitated the procedure of nephelometric inhibition immunoassays in which the residual activity of Ab is measured after absorption with the Ag to be determined. In this procedure for measuring $\alpha_1$-foetoprotein for example, the serum is mixed with anti-$\alpha_1$ foetoprotein antiserum. The Ab:Ag complexes formed are in too low a concentration for them to be separated out by centrifuging, and insolubilised RF or Clq is used to bind with these complexes to remove them from solution. The Ab remaining free in solution are then mixed with $\alpha_1$-foetoprotein and the particle density of the solution, which depends on the residual concentration of Ab, is measured by nephelometry.

CHARACTERISATION

It will be understood that many of the procedures outlined above involving the use of insolubilised RF or Clq, are useful preliminaries in the characterisation of Ab, Ag or Ab:Ag complexes. Some of the procedures do directly result in identification of a particular Ab or Ag, for example, those procedures where the presence of a particular Ab is suspected and subsequently confirmed by adding the specific Ag and detecting the presence of the Ab:Ag complex. The reagents of the invention are very useful reagents in the characterization of Ab, Ag and Ab:Ag complexes, as will be clear from the foregoing description.

Identification (i.e. characterisation) of an antigen is generally effected by various procedures, eg. spectrophotometry to detect the presence of nucleic acids, electron microscopy to identify viruses, immunofluorescence with specific antisera directed against virus or tissue antigens. The last mentioned procedure can be used with insolubilised RF or Clq (eg. agarose beads) having Ab:Ag comlexes bound thereto, i.e. the complex need not first be removed.

For certain purposes, it may be convenient to label insolubilised RF or Clq and this can be effected with, for example, $I^{125}$ or fluorescent or co-enzyme labelling (NADH).

Insolubilised RF and Clq combine not only with Ab:Ag complexes but also with aggregated immunoglobulins. This fact should, of course, be borne in mind when carrying out the procedures described above, as will be clear to those skilled in the art. Aggregated immunoglobulins can be labelled, such as with radioactive iodine or a fluorochrome, and as such can be used in place of labelled Ab:Ag complexes in the analytical procedures described above.

In order that the invention may be more fully understood, the following Examples are given which illustrate various aspects of the invention.

EXAMPLE 1

Coupling of RF or Clq to a solid phase 1 ml of a 25% aqueous solution of glutaraldehyde was added to 5 ml of aminated agarose (AH-Sepharose) which had previously been swollen with a saline solution, in 5 ml of carbonate buffer at pH 8.5. The mixture was stirred for 15 minutes at room temperature and then washed with 100 ml of the carbonate buffer. The mixture was centrifuged, the supernatant was decanted off, and a further 5 ml of the carbonate buffer was added to the solids. While continuously shaking, 1.25 mg of purified RF (or Clq) and sufficient glycine to make the final solution 0.2 molar in glycine, were added. Shaking was continued for 10–12 hours, the solid phase was then separated by centrifuging and washed with physiological saline.

EXAMPLE 2

Preparation of labelled RF or Clq.

200 ml of 50 mM phosphate buffer at pH 7.4 was added to 100 μg of RF (or Clq).

The mixture was divided into 20 μl aliquots and 10 μC $I^{125}$ followed by 50 μg of Chloramine-T were added to each aliquot. Oxidation was allowed to proceed for 30 seconds and the reaction was then terminated by the addition of 50 μl of aqueous sodium metabisulphite solution, containing 50 μg of the salt.

Labelled RF (or Clq) was then separated from the $I^{125}$ by passing the above mixture down a column of Sephadex G25 and eluting the desired labelled material with the above-mentioned phosphate buffer. Eluate fractions were assayed for γ-activity and the fractions having peak activity were pooled, stoppered and frozen until required.

EXAMPLE 3

Separation of Ab:Ag complex

100 μl of insolubilised RF prepared as described in Example 1, were added to 100 μl of a sample containing a naturally occurring Ab:Ag complex in serum. The mixture was shaken for ½ hour at room temperature and was then centrifuged at 3000 g for 5 minutes. It was found that the Ab:Ag complex had been removed from the liquid phase and was attached to the solid phase.

EXAMPLE 4

Determination of tetanus anotoxin + IgG

Rabbit antibodies to tetanus anotoxin were labelled with peroxidase using the technique described by Miles and Hales, *Nature*, 219, 186 (1968).

To 100 μl of serum suspected of containing tetanus anotoxin Ab:Ag complexes, enough of the labelled Ab solution to contain 10 mg of IgG was added. The mixture was shaken at 4° C. overnight. 100 μl of insolubilised RF prepared as described in Example 1, were added to the resulting solution, the mixture was shaken for ½ hour at room temperature and was then centrifuged at 3000 g for 5 minutes. The supernatant was removed with a Pasteur pipette and introduced into a separate tube containing 1 ml of an aqueous solution containing 100 mg of phenol, 30 mg of 4-amino-phanzone and 300 μl of 30% $H_2)_2$ per 100 ml.

The mixed solutions were incubated at 37° C. for 10 minutes. The colour developed at 520 mμ was then colorimetrically estimated. The concentration of tetanus anotoxin was found to be inversely proportional to the peroxidase activity and could be calculated from a calibration curve previously established with solutions of labelled antibody.

EXAMPLE 5

Use of insolubilised RF in automatic analyser of the continuous flow type.

4.0 mg of RF were adsorbed on to 200 mg of 0.8 micron latex particles in a carbonate buffer solution having pH 8.4. The particles were then washed with 0.1% bovine albumin solution to block further absorption.

In an automatic analyser of the continuous flow type, a sample to be tested was aspirated at 0.1 ml/minute and joined a stream flowing at 0.4 ml/minute rabbit antiserum against HPL (dilution 1 in 2000) and this stream was joined by a stream containing $I^{125}$ HPL flowing at 0.4 ml/minute.

The mixed streams were then passed through a mixing coil maintained at 37° C. with a 10 minute time delay and the mixture was then joined by a flow of 0.3 ml/minute of the RF/latex material prepared above containing 100,000 particles/ml.

The mixed stream was again heated for 10 minutes at 37° C. On emerging from the heating bath, the latex particles were separated from the stream and aspirated to waste using any convenient technique, for example the technique used in automated blood typing apparatuses.

The stream was then passed through a gamma counter and the residual counts are recorded. The counts are inversely proportion to the concentration of HPL.

What we claim is:

1. A reagent useful in biological analysis which comprises RF or Clq covalently bonded to a solid phase substrate which is insoluble in aqueous fluids.

2. A method for quantitatively analyzing a fluid sample for an antibody -antigen complex therein, comprising:
   (a) forming a mixture of the sample with a substance selected from the group consisting of RF and Clq, said substance being absorbed onto a solid phase substrate which is insoluble in aqueous fluids;
   (b) allowing the substance on the substrate selectively to react with antibody -antigen complex present in the mixture thereby selectively to bind said complex to said adsorbed substance to form a second complex;
   (c) assaying the second complex to determine the amount of antibody -antigen complex contained therein and thereby determining the amount of antibody -antigen complex present in the sample.

3. A method according to claim 2 wherein the solid phase is a naturally occurring material.

4. A method according to claim 3 wherein the solid phase substrate is aggregated immunoglobulins.

5. A method according to claim 2 wherein the solid phase substrate is a synthetic material.

6. A method according to claim 5 wherein the synthetic solid phase substrate is latex.

7. A method according to claim 2 wherein the substrate is in particulate form.

8. A method according to claim 2 wherein the substrate is the inner surface of a hollow tube.

9. A method according to claim 8 wherein the substrate reacts with Ab:Ag complex by passing the fluid sample through the hollow tube.

10. A method of competitive binding assay by which the presence, in a sample, of a particular antibody, antigen or antibody -antigen complex may be detected, and the amount thereof determined, which comprises the steps of:
    (a) adding to the sample to form a mixture a quantity of the specific antigen or antibody for the antibody or antigen, respectively, to be determined, or a quantity of the antibody -antigen complex to be determined, which said quantity carries an identifying label;
    (b) contacting the mixture with a reagent substance selected from the group consisting of RF and Clq, said substance being adsorbed onto a solid phase substrate which is insoluble in aqueous fluids;
    (c) separating the reagent substance from the mixture; and
    (d) measuring by the identifying label the amount of labelled antibody, antigen, or antibody -antigen complex remaining in the mixture or separated with the reagent, thereby determining the presence and amount of antibody, antigen or antibody -antigen complex in the original sample.

11. A method for quantitatively analyzing an aqueous biological fluid sample for antibody or antigen therein, comprising:
    (a) adding to the sample the appropriate antibody or antigen, respectively, to form antibody -antigen complex;
    (b) forming a mixture of the sample with a substance selected from the group consisting of RF and Clq, the substance being adsorbed onto a solid phase substrate which is insoluble in aqueous fluids;
    (c) allowing the substance on the substrate selectively to react with antibody -antigen complex present in the mixture thereby selectively to bind the complex to the substance; and
    (d) assaying the substance to determine the amount of antibody -antigen complex bound thereto and thereby determining the amount of antibody or antigen present in the sample.

12. A method according to claim 11 wherein the solid phase is a naturally occurring material.

13. A method according to claim 12 wherein the solid phase substrate is aggregated immunoglobulins.

14. A method according to claim 11 wherein the solid phase substrate is a synthetic material.

15. A method according to claim 14 wherein the synthetic solid phase substrate is latex.

16. A method according to claim 11 wherein the substrate is in particulate form.

* * * * *